United States Patent [19]

Cook et al.

[11] Patent Number: 4,745,064

[45] Date of Patent: May 17, 1988

[54] PROCESS FOR THE DEGRADATION OF S-TRIAZINE DERIVATIVES IN AQUEOUS SOLUTIONS

[75] Inventors: Alasdair M. Cook, Wädenswil; Ralf Hütter, Gockhausen, both of Switzerland

[73] Assignee: Ciba-Geigy Corporation, Ardsley, N.Y.

[21] Appl. No.: 665,408

[22] Filed: Oct. 26, 1984

[30] Foreign Application Priority Data

Nov. 4, 1983 [CH] Switzerland ............... 5968/83

[51] Int. Cl.$^4$ ............... C12N 1/20; C12P 39/00; C12P 5/02; C12P 17/00
[52] U.S. Cl. ............... 435/253; 435/42; 435/117; 435/120; 435/167; 435/822; 435/262; 210/600
[58] Field of Search ............... 435/117, 120, 167, 253, 435/822, 262, 42; 210/600

[56] References Cited

U.S. PATENT DOCUMENTS

| | | | |
|---|---|---|---|
| 3,926,795 | 12/1975 | Saldick | 210/11 |
| 4,274,955 | 6/1981 | Zeyer et al. | 435/122 |
| 4,415,658 | 11/1983 | Cook et al. | 435/253 |

FOREIGN PATENT DOCUMENTS 2127006  2/1984  United Kingdom ............... 210/11

OTHER PUBLICATIONS

Cook et al., Journal Agric. Food Chem., 32, 581–585, (1984).
Cook et al., Chem. Abstract, 96, 167981q, (1982).
R. W. Couch, Proc. South Weed Sc. Soc., 18, 623–631, (1965).
European Search Report in European application 0141784.
Cook et al., FEMS Symp., 12, 237–249, (1981).

Primary Examiner—Thomas G. Wiseman
Assistant Examiner—Robin L. Teskin
Attorney, Agent, or Firm—Karl F. Jorda; Irving N. Feit

[57] ABSTRACT

The invention relates to a novel microorganism of the genus *Rhodococcus*, to the use thereof in a process for the microbiological degradation of amino-s-triazines and cyanuric acid in wastewaters, as well as to a process for the microbiological degradation of s-triazine derivatives to biomass or to degradation products such as $NH^{30}_4$ and/or chloride, which comprises the combined use of said microorganism with *Pseudomonas* spp.

12 Claims, No Drawings

PROCESS FOR THE DEGRADATION OF S-TRIAZINE DERIVATIVES IN AQUEOUS SOLUTIONS

The present invention relates to a novel microorganism of the genus Rhodococcus, to the use thereof in a process for the microbiological degradation of amino-s-triazines and of cyanuric acid in waste-waters, as well as to a process for the microbiological degradation of s-triazines to biomass or to degradation products such as $NH_4^+$ or chloride using a combination of said microorganism and Pseudomonas ssp.

Aqueous solutions which contain, inter alia, chloro-s-triazines, amino-s-triazines and (cyclo)alkylamino-s-triazines as impurities are formed continually in the large-scale production of 1,3,5-triazines (s-triazines) in the chemical industry. Such waste-waters are an environmental nuisance on account of the s-triazine derivatives which are only slowly degradable in nature. A pretreatment, however, constitutes a task involving extremely high costs and a correspondingly high consumption of energy, and one which it has so far not been possible to solve satisfactorily. s-Triazine derivatives present in waste-waters can be partially converted by hydrolysis at elevated temperature. In general, however, residual s-triazine derivatives originating from production are present in very dilute solutions, so that it is scarcely possible to degrade them by chemical means.

Accordingly, when seeking methods of purifying dilute waste-waters of this kind, efforts are being continually made to develop microbiological processes which achieve a high biodegradability in each stage of the stepwise degradation of s-triazine derivatives.

Throughout this specification, only such efforts and reaction steps shall be discussed. Unimportant side reactions with very much lower reaction rates will not be specifically mentioned.

The first part of this invention relates to different aspects of a microbiological partial degradation of amino-s-triazines of the formula Ia, wherein $R_1$ is a chlorine atom or an $NH_2$ group and $R_2$ is hydrogen or an aliphatic or cycloaliphatic hydrocarbon radical containing not more than 4 carbon atoms, to corresponding ammelines of the formula Ib and to ammelides of the formula Ic:

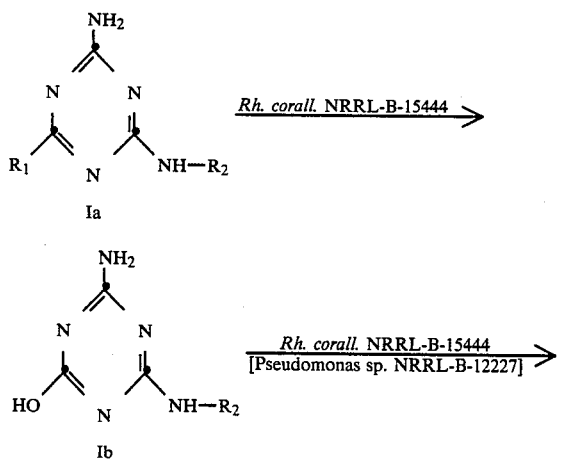

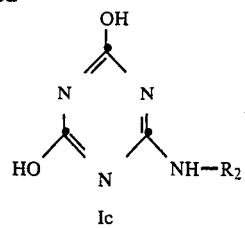

An object of the present invention is the novel microorganism *Rhodococcus corallinus*, strain NRRL B-15444, which originates from soil samples taken from Agricultural Research Stations of CIBA-GEIGY AG, where fields under different cultivation (apples, vines, maize) had been treated over several years (from 4 to 19 years) with Simazine (2-chloro-4,6-bis[ethylamino]-s-triazine) and/or Atrazine (2-chloro-4-ethylamino-6-isopropylamino-s-triazine). This bacterial strain was deposited with the Agricultural Research Culture Collection (NRRL) in Peoria, Ill. 61604, USA, on 13th June 1983. Rh. corallinus NRRL B-15444 is able to deaminate 2,4-diamino-s-triazine derivatives, and to dechlorinate 2-amino-4-chloro-s-triazine derivatives, of the formula Ia, and thus to convert them into corresponding ammeline derivatives of the formula Ib and, in a partly parallel but mainly subsequent reaction, into ammelide derivatives of the formula Ic.

Where $R_2$ is hydrogen, *Rh. corallinus* NRRL B-15444 degrades the ammelide I further, via the step of cyanuric acid, to biomass. The invention also encompasses the mutants of *Rh. corallinus* NRRL B-15444, which are capable of the same degradation reactions.

Pseudomonas spp. and Sporothrix spp. are already known which, as indicated in the above scheme, are able to convert amino substituents in s-triazines to hydroxyl groups, i.e. which are able to degrade amino-s-triazines to corresponding ammelines and ammelides. Surprisingly, the discovery of the novel microorganism *Rh. corallinus* NRRL B-15444 permits access to the microbiological degradation of chloro-s-triazines and thus makes possible for the first time* the biological elimination of the chlorine atom and the formation of the corresponding ammelines of the formula Ib. *Rh. corralinus* NRRL B-15444 has at the same time the advantageous property of cleaving cyanuric acid, a product which constitutes one of the last conversion products in the degradation chain of s-triazines, and of converting it via degradation products such as ureas, biuret, $NH_4^+$, into biomass.

*A publication by Couch et al. (Proc. South Weed Sc. Soc. 1965, Vol. 18, p. 623) on a possible dechlorination of Atrazine using a fungus provides only insufficient particulars for reproducing the experiment and has achieved no importance in practice).

Accordingly, a further object of the invention is a process for the microbiological conversion of 2-amino-s-triazine derivatives of the formula Ia into corresponding ammelines of the formula Ib and ammelides of the formula Ic with the aid of the micro-organism *Rh. corallinus* NRRL B-15444, and the corresponding mutants thereof, under aerobic conditions.

A further object of the invention is also a process for the total microbiological degradation of cyanuric acid with the aid of *Rh. corallinus* NRRL B-15444 and the corresponding mutants thereof, under aerobic conditions.

In the formulae Ia/Ib above, the substituent $R_2$ will be understood as meaning in particular hydrogen, ethyl, isopropyl and cyclopropyl.

Among the compounds of formula I which are very important for actual practice, particular mention is made of 2-amino-4-ethylamino-6-chloro-s-triazine which is biologically very readily formed by deethylating 2,4-bis(ethylamino)-6-chloro-s-triazine (Simazine) and deisopropylating 2-chloro-4-ethylamino-6-isopropylamino-s-triazine (Atrazine) (Wichman and Byrnes, Weed. Sc. 1975, Vol. 23, 488-453) and is detected in rivulets and watercourses originating from fields treated with chloro-s-triazine herbicides (Muir and Baker, J. Agric. Food Chem. 1976, Vol. 24, 122-125).

The microorganism to be used in the practice of this invention is first cultured on a suitable growth medium and then added to aqueous solutions of the substrates to be degraded, or it is cultured direct on media which contain the substrates to be degraded.

The growth of *Rh. corallinus* NRRL B-15444 is promoted by the presence of certain amounts of salts such as sulfates or phosphates of alkali metals (K, Na), alkaline earth metals (Ca, Mg) or transition metals (Fe) as well as alkali molybdates.

A suitable growth medium has for example the following composition:

| | |
|---|---|
| potassium phosphate buffer, pH 7.3 | 10 mM |
| magnesium sulfate heptahydrate | 0.25 mM |
| trace element solution of Pfennig and Lippert (Arch. Microbiol. 55, 246, 1966), supplemented with 100 mg of calcium chloride dihydrate per liter | 5 ml/l |
| glycerol | 10 mM |
| nitrogen source | 2.5 mM of $N_2$ |

A suitable carbon source is e.g. glycerol, fructose, D-gluconate, acetate, fumarate, benzoic acid, salicyclic acid, m-hydrobenzoic acid and the like (q.v. Table 2.2 below).

The s-triazines of the formulae Ia and Ib are used as nitrogen sources, including e.g. 2-amino-4-ethylamino-6-chloro-s-triazine, melamine, 2,4-diamino-6-cyclopropylamino-s-triazine or 2,4-diamino-6-hydroxy-s-triazine.

ISOLATION AND ENRICHMENT

The archetype of the microorganism employed is obtained from waste-water and soil samples and selected by further culturing.

1. Isolation 1.1 The wastewater samples were centrifuged for 10 minutes at $+4°$ C. (20,000 g). The supernatant fluid was discarded and the residual deposit (pellet) was resuspended in a buffer solution (10 mM of potassium phosphate buffer containing 0.25 mM of magnesium sulfate, pH 7.3), filtered and additionally washed twice with buffer. The pellet was then suspended in a buffered salts solution, for example in the growth medium described above, and used as inoculum.

1.2 Samples (5 g) of soils from different CIBA-GEIGY Research Stations in Switzerland that had been treated for several years with s-triazine herbicides were shaken at 30° C. for 1 hour in 100 ml of the buffer solution described in 1.1 and then allowed to settle. The supernatant fluid was filtered through a Whatman No. 1 filter and the filtrate was further processed as described in 1.1 for use as inoculum.

2. Enrichment

Samples (3 ml) of solution, containing 2.5 mM of nitrogen (in the form of s-triazines), 5 mM of glucose, 5 mM of succinate, 10 mM of glycerol and 0.4 ml of inoculum solution, were sealed in culturing tubes and incubated at 30° C. for 1 to 3 days in an absolutely nitrogen-free atmosphere in a container filled with 20% (v/v) of oxygen and 80% (v/v) of helium, under a pressure of about $8 \times 10^4$ Pa. Samples taken therefrom were transferred to agar plates and selected and isolated after positive testing.

CHARACTERISATION OF THE NOVEL MICRO-ORGANISM RHODOCOCCUS CORALLINUS NRRL B-1544

1. General parameters and microscopy

*Rhodococcus corallinus* is gram-positive, oxidase-negative and grows preferably at 20° to 45° C. in a preferred pH range from 6 to 8. It forms dark red colonies and individual mutants also occur in lighter colours. In s-triazine derivatives of the formula Ia, its enzyme system is able to replace the Cl atom by a hydroxyl group. As nitrogen source it is able to utilise the free amino groups of the s-triazine derivatives of the formulae Ia and Ib, including melamine, ammeline, ammelide, 2,4-diamino-6-chloro-s-triazine, cyanuric acid, biuret, urea, $NH^+_4$; and as carbon source it can utilise for example glycerol, acetic acid, ethanol etc.

Under an optical light microscope, *Rhodococcus corallinus* is seen as a non-motile rod of 1-2 μm which, after cell division, frequently occurs in the V- or Y-forms. In an electron micrograph the microorganism appears in the V-form which, in accordance with the gram-positive characteristic, shows the flat surface and, in addition, the cell division ring.

2. Biochemical characterisation and classification of the novel microorganism

BIOCHEMICAL TESTS 2.1 Two commercially available systems are used for the general biochemical characterisation and classification of *Rhodococcus corallinus* NRRL B-15444. They provide general information on the characteristics of gram-positive organisms.

| "Oxi/Ferm Tube" and "Enterotube II" (Roche) Diagnosis | |
|---|---|
| Characteristics: ++ both tests positive − − both tests negative | |
| anaerobic dextrose degradation | − − |
| gas formation during anaerobic dextrose degration | |
| lysine decarboxylase | − − |
| ornithine decarboxylase | − − |
| $H_2S$ formation | − − |
| indole formation | − − |
| adonitol degration | − − |
| lactose degradation | − − |
| arabinose degradation | − − |
| sorbitol degradation | − − |
| acetoin formation | − − |
| dulcitol degradation | − − |
| phenyl alanine deeaminase | − − |
| urease | ++ |
| Simmons citrate utilisation | − − |
| arginine dihydrolase | − − |
| $N_2$ production | − − |
| xylose degradation | − − |
| aerobic dextrose degradation | − − |
| 2.2 Characterization (in accordance with H. Seiler, J. General Microbiol. (1983) 129, 1433-1471) | |

| -continued "Oxi/Ferm Tube" and "Enterotube II" (Roche) Diagnosis | |
|---|---|
| Properties | |
| acetate as C-source | ⎫ |
| propionate as C-source | ⎬ + |
| valerate as C-source | ⎫ |
| capronate as C-source | ⎬ + |
| adipate as C-source | ⎫ |
| levulinate as C-source | ⎪ |
| glyoxalate as C-source | ⎬ |
| glycine as C-source | ⎪ − |
| xanthine hydrolysis | ⎭ |
| D-xylose as C-source | ⎫ |
| D-galactose as C-source | ⎬ − |
| acid formation from D-glucose | ⎫ |
| acid formation from sucrose | ⎬ |
| acid formation from lactose | ⎫ |
| acid formation from starch | ⎬ |
| acid formation from dextrin | ⎭ − |
| anaerobic reaction | − |
| 5-aminovalerate as C-source | − |
| succinate as C-source | + |
| adipate as C-source | − |
| citrate as C-source | + |
| D-gluconate as C-source | + |
| L-leucine as C-source | − |
| L-asparagine as C-source | − |
| L-aspartate as C-source | − |
| D-ribose as C-source | − |
| L-arabinose as C-source | − |

PRESERVATION OF RHODOCOCCUS CORALLINUS NRRL B-15444

The following methods are suitable for preserving the novel strain:

(a) Keeping the biomass of the strain on slant agar (according to the growth medium described above; N-source of the 2-chlorotriazine of the formula Ia mandatory), and (b) lyo-ampoules (in addition to the C-source, the presence of small amounts of 2-chlorotriazine as desired N-source is mandatory). The culture is centrifuged off from the nutrient solution and the biomass is resuspended in ¼ to ⅓ volumes of 15% skimmed milk and lyophilised.

Mutants of the novel strain can form spontaneously or mutants can be prepared artificially, which latter mutants, like the natural strain, are able to degrade compounds of the formulae Ia and Ib in aqueous solution and to produce biomass. Mutants can also be produced by chemical means, for example with specific guanidine derivatives, e.g. N-methyl-N-nitrosoguanidine, or an alkali nitrite such as sodium nitrite, or by physical means, e.g. by ultra-violet, X-ray or radioactive irradiation.

In the second part, the present invention relates to various aspects of a total microbiological degradation of amino-s-triazines of the formulae Ia and Ib, wherein $R_1$ is a chlorine atom or an $NH_2$ group and $R_2$ is hydrogen or an aliphatic or cycloaliphatic hydrocarbon radical containing not more than 4 carbon atoms, principally to biomass by combined use of the microorganisms (a) *Rhodococcus corallinus* NRRL B-15444 alternatively with (b) Pseudomonas sp NRRL-B-12228 and/or (c) Pseudomonas sp. NRRL-B-12229, optionally with the further addition of (d) Pseudomonas NRRL-B-11308 and/or (e) *Sporothrix schenkii* NRRL-Y-11307.

The Pseudomonas strains referred under (b) and (c) and their degradation particulars are known from EP published patent specification No. 47 719 (or from the equivalent ZA patent specification No. 81/6236).

The microorganisms referred to under (d) and (e) and their degradation particulars are known from DE-OS No. 29 23 794 (or from the equivalent GB patent specification No. 2 025 919).

As described hereinafter, mixed cultures of the above-mentioned microorganisms achieve greater degradation results than were to have been expected from the addition of the different degradation performances of the individual microorganisms.

Accordingly, the invention also relates to a combined microbiological process by means of which s-triazine derivatives of the formula Ia or Ib present in aqueous solutions, e.g. wastewaters, are totally degraded, under aerobic conditions, by jointly treating said solutions with *Rhodococcus corallinus* NRRL B-15444, or with mutants thereof, together with Pseudomonas sp. NRRL B-12228 or Pseudomonas sp. NRRL B-12229, or mutants thereof, optionally with the further addition of Pseudomonas NRRL B-11308 and/or *Sporothrix schenkii* NRRL Y-11307, or mutants thereof.

By means of the process of this invention using, under aerobic conditions, a combination of *Rhodococcus corallinus* with at least one of the two Pseudomonas strains for treating waste-waters which contain the s-triazine derivatives of both the formula Ia and of the formula Ib, the said compounds are totally degraded and used to form biomass.

The novel microorganism *Rhodococcus corallinus* NRRL-B-15444 and the known strains Pseudomonas sp. NRRL B-12228 and Pseudomonas sp. NRRL B-12229 are used in the process of this invention for the microbiological purification of aqueous solutions containing compounds of the formula Ia and/or Ib, which process comprises growing the microorganism *Rhodococcus corallinus* NRRL-B-15444, or a mutant derived therefrom, and Pseudomonas sp. NRRL B-12228 and/or Pseudomonas sp. NRRL B-12229, or a mutant thereof which is able to produce biomass, in the presence of growth-promoting inorganic salts, in the temperature range from about 20° to 40° C. and at a pH value in the range from about 6 to 8.5, and, if desired, isolating said biomass.

In the process for treating aqueous solutions, the above-mentioned microorganisms degrade the compounds of the formula Ia and/or Ib present in these solutions while consuming oxygen. The compounds may also be present in the solutions in concentrations up to saturation.

For the fermentative treatment of the solutions, the pH is adjusted to values in the range from about 6 to 8, preferably to 7, by the addition of a buffer solution, for example phosphate buffer, or of an aqueous base, e.g. aqueous sodium or potassium hydroxide solution.

The growth of the microorganisms is promoted by the presence of certain salts such as sulfates or phosphates of alkali metals (K, Na), alkaline earth metals (Ca, Mg) or transition metals (Fe) as well as borates or molybdates of alkali metals.

Preferred inorganic salts are for example disodium or dipotassium hydrogen phosphate, sodium or potassium hydrogen phosphate, magnesium and iron sulfate, and potassium and calcium chloride. Zinc, manganese and copper sulfate, sodium molybdate and borax may additionally be added in small amounts. The presence of other salts (e.g. alkali metal chlorides) in concentrations of up to 4% does not interfere with the degradation.

For the purification of aqueous solutions which contain triazine derivatives of the formula Ia and/or Ib, a carbon source, for example glycerol, acetic acid or ethanol, is added to the solutions on account of their low content of utilisable carbon.

The growth of the cultures takes place in these media under aerobic conditions, for example in an atmosphere of oxygen or air, namely by shaking or stirring in shaking flasks or fermenters. Culturing can be effected in a temperature range from about 20° to 40° C., preferably from about 30° to 35° C.

Growth of the cultures can be effected batchwise, for example by single or repeated addition of nutrient solution, or continuously by constant addition of nutrient solution. The size of the reaction vessel is of no consequence for the reaction course as long as the above-mentioned conditions are kept.

It is preferred to grow the cultures in several steps by first preparing one or more precultures, e.g. in a liquid culture medium, with which precultures the main culture is then inoculated. A preculture can be prepared for example by transferring a sample containing cell material of the respective microorganisms, which has been kept for example on slant agar, to a sterile solution which contains s-triazines of the formulae Ia and/or Ib, and incubating the batch for several days at 28°–30° C. Fresh nutrient solution is inoculated with this first preculture and the batch is again incubated for several days at the same temperature.

The course of the growth can be followed analytically during fermentation, e.g. by measuring the decrease in concentration of the s-triazines in the culture solution or by measuring the protein content, which serves a reference value of the growth of the respective strain, and also gravimetrically on the basis of the dry weight of the biomass formed.

The biomass can be processed by one of the numerous methods described in European patent specification No. 10 243 and converted into high grade fertilisers which contain no contaminating metal ions.

Biomass is defined in this context as comprising all cell systems in the living state, e.g. that of replication or resting, in the state of partial or complete death, or already in a state of enzymatic decomposition or of decomposition by foreign cultures, which cell systems are based on the microorganisms of the present invention.

The biomass of defined and reproducible composition obtained by the process of this invention can be used for example as animal feed additive. As mentioned, it can also be used as suspension or processed to fertiliser, for example after dehydration or pasteurisation. The biomass can also be used as starting material for the production of biomass with a high heat content (composition: about 70% of methane, 29% of carbon dioxide and 1% of hydrogen, heat content about 5500–6500 kcal/m$^3$), for example by anaerobic fermentation in fermentation towers. The residue (sludge) from the production of biogas is also a high grade fertiliser which, compared with the original biomass, is highly enriched with nitrogen.

The invention is illustrated by the following Examples.

EXAMPLE 1

(Preparation of the preculture)

1 sample of the microorganism of the strain *Rhodococcus corallinus* NRRL B-15444 is incubated in a test tube containing 3 ml of nutrient solution with 0.5 mM of 2-amino-4-ethylamino-6-chloro-s-triazine, and the batch is incubated for 96 hours at 30° C. and 4 rps. 1 ml of this preculture is introduced into a second shaking bottle containing 100 ml of nutrient solution with 0.5 mM of 2-amino-4-ethylamino-6-chloro-s-triazine and the batch is incubated for 96 hours at 28° C. and 4 rps.

EXAMPLE 2

Degradation of 2-amino-4-ethylamino-6-chloro-s-triazine to 2,6-dihydroxy-4-ethylamino-s-triazine by growing cultures of *Rhodococcus corallinus* NRRL-B-15444

A laboratory fermenter is charged with 10 liters of non-sterilised or heat-sterilised (sterilisation for 20 minutes at 120° C.) nutrient solution containing 0.5 mM of 2-amino-4-ethylamino-6-chloro-s-triazine. A sample containing about 500 ml of the second preculture of the strain *Rhodococcus corallinus* NRRL B-15444 is added and the following conditions are kept: pH 7, which is kept by stirring in 4N aqueous sodium hydroxide solution and 1N hydrochloric acid respectively; temperature: 28° C.; rate of addition of air: 0.26 l/min. The strain grows on pure 2-amino-4-ethylamino-6-chloro-s-triazine as sole source of nitrogen. The s-triazine is completely degraded after about 200 hours. The biomass obtained is in the form of a mixture of single cells or aggregates of different size and can be isolated by sedimentation or centrifuging.

EXAMPLE 3

Degradation of 2-amino-4-ethylamino-6-chloro-s-triazine to 2,6-dihydroxy-4-ethylamino-s-triazine by growing cultures of *Rhodococcus corallinus* NRRL B-15444

A sample of the strain *Rhodococcus corallinus* NRRL B-15444 is taken from a slant agar culture on base agar and inoculated into a growth medium of the following composition:

| | |
|---|---|
| potassium phosphate buffer, pH 7.3 | 10 mM |
| magnesium sulfate heptahydrate | 0.25 mM |
| nutrient solution of Pfennig and Lippert (Arch. Microbiol. 55, 246, 1966), supplemented with 100 mg of calcium chloride hydrate per liter | 5 ml/l |
| glycerol | 10 mM |
| 2-amino-4-ethylamino-6-chloro-s-triazine | 2.5 mM |

60 ml portions of this culture solution are each cultured in 500 ml Erlenmeyer flasks on a gyrotatory shaker (2–3 rps) at 30° C. for 75 hours. Samples are taken at intervals of 24 hours and measurements of the turbidity of the protein content and of the concentration of the nitrogen source are made.

| Protein g/mole of substrate | Result: Nitrogen utilisation mole/mole of substrate | Protein g/mole of N | Degradation compound mole/mole of substrate |
|---|---|---|---|
| 39 | 1 | 39 | 0–98 |

EXAMPLE 4

Partial degradation or total degradation (*) of different s-triazine derivatives by growing cultures of Rhodococcus corallinus NRRL B-15444

In accordance with the experimental procedure of Example 3, further s-triazine derivatives are used as nitrogen sources for testing the degradation properties of Rh. corallinus NRRL B-15444. The s-triazine derivatives are, as indicated, either partially or completely (*) degraded, i.e. substantially to $Cl^-$ and biomass. In this second case, "nd" (not detectable) appears in the last column of the table.

The following abbreviations are employed for s-triazine derivatives:

EOAT=2-ethylamino-4-hydroxy-6-amino-s-triazine (is degraded to EOOT);
IOAT=2-isopropylamino-4-hydroxy-6-amino-s-triazine (is degraded to IOOT);
EOOT=2-ethylamino-4,6-dihydroxy-s-triazine;
IOOT=2-isopropylamino-4,6-dihydroxy-s-triazine;
AAAT(*)=melamine (2,4,6-triamino-s-triazine);
OAAT(*)=2-hydroxy-4,6-diamino-s-triazine (ammeline);
OOAT(*)=2,4-dihydroxy-6-amino-s-triazine (ammelide);
OOOT(*)=cyanuric acid (2,4,6-trihydroxy-s-triazine).

TABLE

| N⁻ source | Protein g/mole of substrate | nitrogen utilisation mole/mole of substrate | Protein g/mole of N | Degradation compound mole/mole of substrate | N⁻ source (conclusion) |
|---|---|---|---|---|---|
| EOAT | 46 | 1 | 46 | 0.99 | EOOT |
| IOAT | 49 | 1 | 49 | 1.03 | IOOT |
| EOOT | 1 | 0 | 0 | 0 | EOOT |
| IOOT | 1 | 0 | 0 | 0 | IOOT |
| AAAT | 264 | 6 | 44 | nd | nd |
| OAAT | 246 | 5 | 49 | nd | nd |
| OOAT | 184 | 4 | 46 | nd | nd |
| OOOT | 150 | 3 | 50 | nd | nd |

As shown in Example 5 below, the failure of Rh. corallinus NRRL B-15444 to degrade 2-alkylamino-4,6-dihydroxy-s-triazines of the formula Ic (e.g. EOOT and IOOT), where the degradation of 2-chloro-4-amino-6-alkylamino-s-triazine derivatives in this stage comes to a stop, can be converted into a highly efficient process for the total degradation of s-triazine derivatives of the formulae Ia/Ib by using a combination of this microorganism with other microorganisms which are able to utilise such s-triazine derivatives as nitrogen source. Better degradation results are thereby achieved than were to have been expected from the individual values of the separately employed microorganisms.

EXAMPLE 5

Degradation of 2-amino-4-ethylamino-6-chloro-s-triazine to chloride ions and biomass by combined growing cultures of Rh. corallinus NRRL B-15444 and Pseudomonas sp. NRRL B-12228

Samples of the strains Rh. corallinus NRRL B-15444 and Pseudomonas sp. NRRL B-12228 are taken from slant agar cultures on base agar and inoculated jointly into a growth medium of the following composition:

| | |
|---|---|
| Potassium phosphate buffer, pH 7.3 | 15 mM |
| magnesium sulfate heptahydrate | 0.25 mM |
| trace element solution of Pfennig and Lippert (Arch. Microbiol. 55, 246, 1966), supplemented with 100 mg of calcium chloride dihydrate per liter | 5 ml/l |
| glycerol | 10 mM |
| lactic acid | 10 mM |
| 2-amino-4-ethylamino-6-chloro-s-triazine (CEAT) | 2.5 mM |

60 ml portions of this culture solution are each cultured in 500 ml Erlenmeyer flasks on a gyrotatory shaker (2–3 rps) at 30° C. for 75 hours. Samples are taken at intervals of 24 hours and measurements of the turbidity of the protein content and of the concentration of the nitrogen source are made.

| N— source | Protein g/mole of substrate | Result: nitrogen utilisation mole/mole of substrate | Protein g/mole of N | Degradation compound mole/mole of substrate | N— source (conclusion) |
|---|---|---|---|---|---|
| CEAT | 215 | 5 | 43 | nd | nd |

What is claimed is:

1. A biologically pure culture of a microorganism of the genus Rhodococcus corallinus NRRL B-15444.

2. A biologically pure culture of a microorganism of the genus Rhodococcus corallinus NRRL B-15444 and the mutants thereof which, in aqueous solutions of s-triazine derivatives of the formulae Ia or Ib or mixtures thereof,

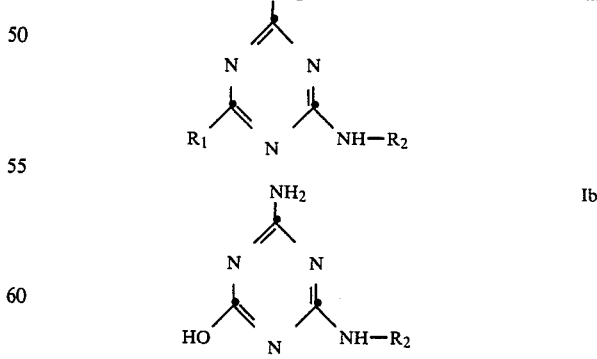

wherein $R_1$ is a chlorine atom or an $NH_2$ group and $R_2$ is hydrogen or an aliphatic or cycloaliphatic hydrocarbon radical containing not more than 4 carbon atoms, are able to form corresponding ammelides of the formula

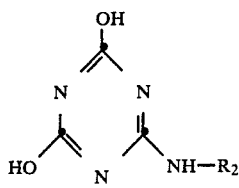

3. A process for degrading s-triazine derivatives of the formulae Ia and Ib

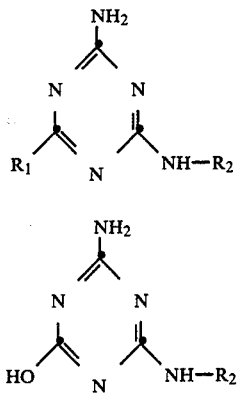

wherein $R_1$ is a chlorine atom or an $NH_2$ group and $R_2$ is hydrogen or an aliphatic or cycloaliphatic hydrocarbon radical containing not more than 4 carbon atoms, in aqueous solutions, which process comprises contacting said solutions with the strain *Rhodococcus corallinus* NRRL B-15444, under aerobic conditions, in the pH range from 6 to 8.

4. A process according to claim 3, wherein $R_2$ is hydrogen, ethyl, isopropyl or cyclopropyl in the formulae Ia and Ib.

5. A process according to claim 3, wherein $R_1$ in formula Ia is a chlorine atom.

6. A process according to claim 3, wherein sulfates or phosphates of alkali metals, alkaline earth metals or transition metals or alkali molybdates are used as inorganic salts which promote the growth of the microorganism.

7. A process according to claim 3, wherein the process is carried out in the temperature range from 20° to 45° C.

8. A process for the microbiological purification of aqueous solutions containing compounds of the formulae Ia or Ib or mixtures thereof.

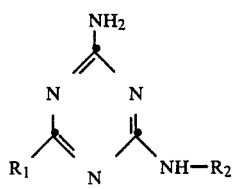

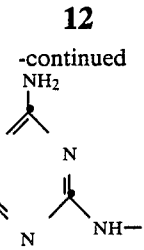

wherein $R_1$ is a chlorine atom or an $NH_2$ group and $R_2$ is hydrogen or an aliphatic or cycloaliphatic hydrocarbon radical containing not more than 4 carbon atoms, which process comprises growing the microorganism *Rhodococcus corallinus* NRRL-B15444, or a mutant derived therefrom, together with Pseudomonas sp. NRRL-B-12228 or Pseudomonas sp. NRRL-B-12229, or mixtures thereof or a mutant thereof which is able to produce biomass, in the presence of growth-promoting inorganic salts, in the temperature range from about 20° to 40° C. and at a pH value in the range from about 6 to 8.5, and, if desired, isolating said biomass.

9. A process according to claim 8, wherein the process is carried out under aerobic conditions in the pH range from 6 to 8.

10. A process according to claim 8, wherein Pseudomonas NRRL B-11308 or *Sporothrix schenkii* NRRL Y-11307 or mixtures thereof are used as additional micro-organisms.

11. A biologically pure culture of an s-triazine degrading mutant of *Rhodococcus corallinus* which has the ability to convert s-triazine derivatives of the formula Ia or Ib or mixtures thereof

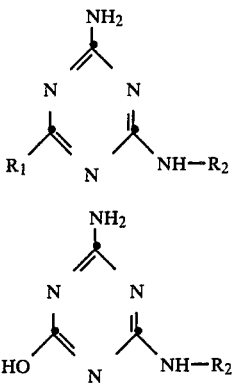

wherein $R_1$ is a chlorine atom or an $NH_2$ group and $R_2$ is hydrogen or an aliphatic or cycloaliphatic hydrocarbon radical containing not more than 4 carbon atoms, to corresponding ammelides of the formula Ic

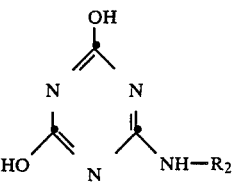

12. A culture according to claim 11 wherein the mutant has the identifying characteristics of *Rhodococcus corallinus* NRRL B-15444.